(12) United States Patent
Milne et al.

(10) Patent No.: US 8,469,906 B2
(45) Date of Patent: *Jun. 25, 2013

(54) THERAPEUTIC MICRO-VIBRATION DEVICE

(76) Inventors: Robert Milne, Las Vegas, NV (US);
Walter J. Spawr, Lake Havasu, AZ (US)

( * ) Notice: Subject to any disclaimer, the term of this patent is extended or adjusted under 35 U.S.C. 154(b) by 1294 days.

This patent is subject to a terminal disclaimer.

(21) Appl. No.: 12/009,087

(22) Filed: Jan. 15, 2008

(65) Prior Publication Data
US 2008/0214969 A1  Sep. 4, 2008

Related U.S. Application Data

(63) Continuation-in-part of application No. 11/121,602, filed on May 4, 2005, now Pat. No. 7,335,170.

(51) Int. Cl.
*A61H 1/00* (2006.01)

(52) U.S. Cl.
USPC .............................. 601/15; 601/67

(58) Field of Classification Search
USPC ............... 601/9, 11, 13, 15, 66, 67, 69, 70, 601/113, 131
See application file for complete search history.

(56) References Cited

U.S. PATENT DOCUMENTS

| | | | |
|---|---|---|---|
| 5,035,235 A | 7/1991 | Chesky | |
| 5,103,806 A | 4/1992 | McLeod et al. | |
| 5,191,880 A | 3/1993 | McLeod et al. | |
| 5,273,028 A | 12/1993 | McLeod et al. | |
| 5,304,207 A | 4/1994 | Stromer | |
| 5,376,065 A | 12/1994 | McLeod et al. | |
| 5,464,436 A | 11/1995 | Smith | |
| 5,562,706 A | 10/1996 | Lauterbach et al. | |
| 5,632,720 A | 5/1997 | Kleitz | |
| 5,645,578 A | 7/1997 | Daffer et al. | |
| 5,830,211 A | 11/1998 | Santana et al. | |
| 6,001,055 A | 12/1999 | Souder | |
| 6,231,497 B1 | 5/2001 | Souder | |
| 6,245,006 B1 | 6/2001 | Olson | |

(Continued)

FOREIGN PATENT DOCUMENTS

| | | |
|---|---|---|
| CA | 2456690 A1 | 2/2003 |
| CN | 1857748 A | 11/2006 |

(Continued)

OTHER PUBLICATIONS

A Chinese Office Action, dated May 17, 2010, from the State Intellectual Property Office of the People's Republic of China for co-pending CN patent application No. 200510121772.1 (6 pages).

(Continued)

*Primary Examiner* — Michael A. Brown
(74) *Attorney, Agent, or Firm* — Schiff Hardin LLP

(57) ABSTRACT

A therapeutic module for relieving pain and providing a curative healing effect includes a motor for rotating at least one magnet to generate a magnetic field, micro-vibrations and audible acoustic tones. A shaft couples the at least one magnet to the motor. The at least one magnet is coupled to the shaft in an offset configuration with respect to a centerline of the shaft thereby generating micro-vibrations in the form of oscillating inertial loads. The therapeutic module includes a light source for generating a photonic light field in an optical light spectrum.

40 Claims, 5 Drawing Sheets

U.S. PATENT DOCUMENTS

| | | | |
|---|---|---|---|
| 6,344,021 | B1 | 2/2002 | Juster et al. |
| 6,461,377 | B1 | 10/2002 | An |
| 6,547,713 | B1 | 4/2003 | Talpo |
| 6,602,275 | B1 | 8/2003 | Sullivan |
| 6,702,837 | B2 | 3/2004 | Gutwein |
| 6,746,473 | B2 | 6/2004 | Shanks et al. |
| 2003/0045770 | A1 | 3/2003 | van Mullekom |
| 2004/0054386 | A1 | 3/2004 | Martin et al. |
| 2004/0147984 | A1 | 7/2004 | Altshuler et al. |
| 2004/0171970 | A1* | 9/2004 | Schleuniger et al. ............. 601/2 |
| 2004/0225339 | A1 | 11/2004 | Yaroslavsky et al. |
| 2004/0260210 | A1 | 12/2004 | Ella et al. |
| 2004/0260212 | A1 | 12/2004 | Cho |
| 2005/0015121 | A1 | 1/2005 | Molina |
| 2005/0108057 | A1* | 5/2005 | Cohen et al. ....................... 705/3 |
| 2005/0182389 | A1 | 8/2005 | LaPorte et al. |
| 2006/0122631 | A1 | 6/2006 | Kertz |

FOREIGN PATENT DOCUMENTS

| | | | |
|---|---|---|---|
| EP | 0204525 | A1 | 12/1986 |
| EP | 1829580 | * | 9/2007 |
| EP | 1829580 | A1 | 9/2007 |
| KR | 2001/0083578 | A | 9/2001 |
| KR | 20010083578 | A | 9/2001 |
| RU | 2195329 | C1 | 12/2002 |
| WO | 9939764 | A2 | 8/1999 |
| WO | 2004066899 | A2 | 12/2004 |
| WO | 2006118608 | A2 | 11/2006 |
| WO | WO2006118608 | * | 11/2006 |

OTHER PUBLICATIONS

An International Search Report for copending International Application No. PCT/US2009/030953.

An International Search Report for copending International Application No. PCT/US2009/030953, Mar. 16, 2009.

Communication from European Patent Office including Extended European Search Report for European Application No. 09702421.0 (7 pages), May 7, 2012.

Klein, Anne: "This MVT Relief device . . . gave me hope" XP002580215 Retrieved from the Internet: URL:http://mvtrelief.com/testimonials.pho?id=4 [retrieved on Feb. 13, 2013].

"Micro-vibration Therapy: Welcome friends . . ."XP002580216 Las Vegas Retrieved from the Internet: URL:http://222.mytherapy.com/home.htm [retrieved on Feb. 13, 2013].

English language translation of CN1857748, Aug. 11, 2006.

English language translation of KR20010083578, Feb. 16, 2000.

State Intellectual Property Office of the People's Republic of China Translation of Notification of the Fifth Office Action in Application No. 200510121772.1 entitled Therapeutic Micro-Vibration Device, Inventor: Robert Milne, et al. dated Jan. 14, 2013.

State Intellectual Property Office of the People's Republic of China Translation of Reexamination Decision in Application No. 200510121772.1 entitled Therapeutic Micro-Vibration Device, Inventor: Robert Milne, et al. dated Sep. 4, 2012.

State Intellectual Property Office of the People's Republic of China Translation of Rejection Decision in Application No. 200510121772.1 entitled Therapeutic Micro-Vibration Device, Inventor: Robert Milne, et al. dated Mar. 23, 2011.

State Intellectual Property Office of the People's Republic of China Translation of Notification of the Fourth Office Action in Application No. 200510121772.1 entitled Therapeutic Micro-Vibration Device, Inventor: Robert Milne, et al. dated May 17, 2010.

State Intellectual Property Office of the People's Republic of China Translation of Notification of the Third Office Action in Application No. 200510121772.1 entitled Therapeutic Micro-Vibration Device, Inventor: Robert Milne, et al. dated Jan. 22, 2010.

State Intellectual Property Office of the People's Republic of China Translation of Notification of the Second Office Action in Application No. 200510121772.1 entitled Therapeutic Micro-Vibration Device, Inventor: Robert Milne, et al. dated Sep. 11, 2009.

State Intellectual Property Office of the People's Republic of China Translation of Notification of the First Office Action in Application No. 200510121772.1 entitled Therapeutic Micro-Vibration Device, Inventor: Robert Milne, et al. dated Feb. 20, 2009.

State Intellectual Property Office of the People's Republic of China Translation of Notification of the First Office Action in Application No. 200980105458.0 entitled Therapeutic Micro-Vibration Device, Inventor: Robert Milne, et al. dated Jun. 13, 2012.

European Patent Office Communication pursuant to Article 94(3) EPC in Application No. 05 848 831.3 entitled Therapeutic Micro-Vibration Device, Inventor: Robert Milne, et al. dated Oct. 31, 2012.

European Patent Office extended European search report in Application No. 05 84 8831.3 entitled Therapeutic Micro-Vibration Device, Inventor: Robert Milne, et al. dated Jun. 4, 2010.

European Patent Office extended European search report in Application No. 09702421.0 entitled Therapeutic Micro-Vibration Device, Inventor: Robert Milne, et al. dated May 7, 2012.

Translation of Korean Intellectual Property Office Notice of Office Action in Application No. 2007-7025544 entitled Therapeutic Micro-Vibration Device, Inventor: Robert Milne, et al. dated Sep. 14, 2009.

Translation of Korean Intellectual Property Office Notice of Final Rejection in Application No. 10-2007-7025544 entitled Therapeutic Micro-Vibration Device, Inventor: Robert Milne, et al. dated Jun. 19, 2009.

Translation of Korean Intellectual Property Office Notice of Office Action in Application No. 2007-7025544 entitled Therapeutic Micro-Vibration Device, Inventor: Robert Milne, et al. dated Sep. 24, 2008.

* cited by examiner

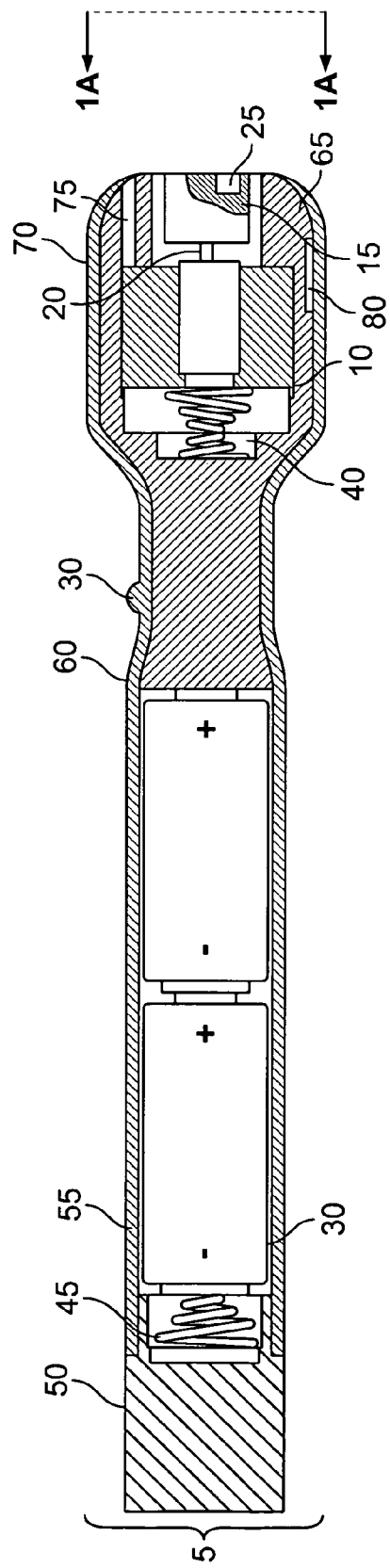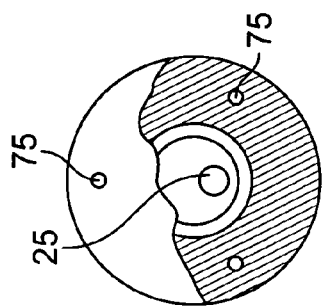
FIG. 1
FIG. 1A

THERAPEUTIC MICRO-VIBRATION DEVICE

CROSS REFERENCE TO RELATED APPLICATIONS

This is a continuation-in-part application of U.S. application Ser. No. 11/121,602, filed May 4, 2005, now U.S. Pat. No. 7,335,170, which is hereby incorporated by reference in its entirety.

FIELD OF THE INVENTION

The embodiments of the present invention relate to a medical therapy device that utilizes micro-vibratory massaging action with magnetic and photonic light beam fields, accompanied by sound waves, to induce an increase in cellular energy thereby providing pain reduction and healing in living cells.

BACKGROUND OF THE INVENTION

The use of vibrating devices for massaging painful areas on the human body by stimulating blood flow has long been considered beneficial. Photonic light beam therapy, typically utilizing laser beams, for relieving pain and healing anomalous tissue has also been used with varying levels of success. Static and pulsating magnetic field therapy has been used for many years throughout the world with varying levels of success. Sound waves, including music, for relieving tension and soothing the human body have also been used. There is, however, no prior art that discloses or suggests coordination and integrative merging of the above-identified technologies in such a manner to bring about a synergistic enhancement of all four technologies.

The prior art discloses the use of electrically driven vibrators and massagers that produce vibration that stimulates circulation to affected tissues. Also, vibration and impact devices are known in the art to encourage bone growth. For example, U.S. Pat. No. 5,273,028 to Kenneth J. McLeod discloses an apparatus for stimulating bone growth in a living organism by transmitting vertical vibrations through a plate upon which the person stands. U.S. Pat. Nos. 5,103,806, 5,376,065 and 5,191,880 also to McLeod, claim methods for preventing osteopenia while promoting growth and healing of bone tissue, including fractured bones, by subjecting the bone to a mechanical load.

U.S. Pat. No. 6,245,006 to Olson describes magnetic therapy as an established and reliable technology. U.S. Pat. No. 5,632,720 to Kleitz describes a motor driven magnetic massage wand which, during use, comes no closer than 18 inches to the human body. Therefore, the wand does not need to come into physical contact with the body. The wand uses a magnetic field between 950 to 1050 gauss in intensity to facilitate an increase in blood flow.

U.S. Pat. No. 6,602,275 to Sullivan discloses the use of dispersed photon light waves at 470 nm, 630 nm and 880 nm to stimulate the human healing process by reducing inflammation, stimulating and rebalancing the electromagnetic energy field surrounding living organisms and detoxifying organs and tissue.

U.S. Pat. No. 5,035,235 to Chesky discloses the use of musical sound waves as therapy for chronic and acute pain. U.S. Pat. No. 5,645,578 to Daffer et al also describes a therapeutic device that utilizes musical tones.

Many of the prior art devices are large and expensive and may require a patient to lie down on the device for several hours. Some of the prior art devices are handheld devices but use only one or two of the subject technologies. For instance, U.S. Pat. Nos. 6,001,055 and 6,231,497 to Souder claim a handheld device with one or more rotating permanent magnets and a vibrating massaging feature. None of the prior art devices utilize or suggest the use of mechanical micro-vibration, photon, sonic, and magnetic technologies in a handheld device which provides pain relief in a short period of time (e.g., seconds) from application.

The prior art is thus characterized by numerous disadvantages which are addressed by the embodiments of the present invention. The embodiments of the present invention minimize, and in some cases eliminate, the above-mentioned disadvantages and shortcomings by utilizing integration of technologies in a convenient handheld device. Clinical trials confirm nearly instant pain relief for patients.

BRIEF DESCRIPTION OF THE INVENTION

Accordingly, the present disclosure describes a handheld pain relieving device that includes an integrative combination of vibration, photon, magnetic and sonic technologies, that can be conveniently directed or applied to an area of the human body suffering from pain or other affliction. In one embodiment, a system for relieving pain and providing a curative healing effect includes a handheld pain relieving device and a controller operatively coupled to the handheld pain relieving device to control one or more parameters of the handheld pain relieving device.

In one aspect, the device includes a motor that produces micro-vibrations and audible signals and drives one or more permanent magnets or electromagnets and one or more light sources. Importantly, the motor produces a very small electromagnetic field so as not to interfere with the magnetic flux generated by the one or more permanent magnets or electromagnets. An applicator end of the device is placed in contact with, or proximate to, an area of the body suffering from pain or related affliction. During clinical trials, the combination of the magnetic, photon, vibration and sound technologies proved to provide pain relief in very short time periods.

In another aspect, a therapeutic module for relieving pain and providing a curative healing effect is provided. The therapeutic module includes a motor for rotating at least one magnet to generate a magnetic field, micro-vibrations and audible acoustic tones. A shaft couples the at least one magnet to the motor. The at least one magnet is coupled to the shaft in an offset configuration with respect to a centerline of the shaft thereby generating micro-vibrations in the form of oscillating inertial loads. The therapeutic module includes a light source for generating a photonic light field in an optical light spectrum.

In another aspect, a system for relieving pain and providing a curative healing effect includes at least one therapeutic module and a controller operatively coupled to the therapeutic module. The therapeutic module includes at least one magnet coupled to a shaft in an offset configuration with respect to a centerline of the shaft. A motor is coupled to the shaft for rotatably driving the at least one magnet to generate a dynamic magnetic field which penetrates living tissue and micro-vibrations including oscillating inertial loads resulting from rotation of the at least one magnet about the centerline. The therapeutic module also includes a light source for generating a photonic light field in an optical light spectrum. The controller is configured to control the therapeutic module to facilitate relieving pain and providing a curative healing effect.

In another aspect, a method is provided for administering pain relief with at least one therapeutic module. The method includes rotating at least one magnet to generate a magnetic field. The magnetic field includes a moving circular magnetic field pattern with a centerline of the magnetic field parallel to a centerline of a rotating shaft coupling the at least one magnet to a motor. A photonic light field is generated in an optical light spectrum. The photonic light field is directed into the magnetic field. Micro-vibrations are generated by rotating the at least one magnet coupled to the shaft in an offset configuration in a circular pattern defined about a centerline of the shaft. Audible acoustic tones are also generated. The at least one therapeutic module is placed in contact with, or proximate to, a pain area on a human or animal body.

In another aspect, a therapeutic device for relieving pain and providing a curative healing effect is provided. The therapeutic device includes a motor for rotating at least one magnet to generate a magnetic field, micro-vibrations and audible acoustic tones. A shaft couples the at least one magnet to the motor. The at least one magnet is coupled to the shaft in an offset configuration with respect to a centerline of the shaft thereby generating micro-vibrations in the form of oscillating inertial loads. The therapeutic device also includes a light source for generating a photonic light field in an optical light spectrum. In a further aspect, a system for relieving pain and providing a curative healing effect is provided. The system includes the therapeutic device and a controller operatively coupled to the therapeutic device. The controller is configured to control the therapeutic device to facilitate relieving pain and providing a curative healing effect.

In another aspect, a handheld therapeutic device for relieving pain and providing a curative healing effect is provided. The handheld therapeutic device includes a plurality of magnets coupled to a shaft in an offset manner such that the plurality of magnets rotate in a circular pattern defined about a centerline of the shaft. The plurality of magnets are spaced unevenly about the centerline. The handheld therapeutic device includes a motor for rotatably driving the plurality of magnets to generate a dynamic magnetic field, which penetrates living tissue, and micro-vibrations in the form of oscillating inertial loads resulting from the rotation of the plurality of magnets about the centerline of the shaft. At least one light source is configured to generate a photonic light field in an optical light spectrum and a speaker is configured to produce audible acoustic tones.

The device is unique in the well-established field of magnetic therapy, wherein stationary, static and/or multiple magnets are used, and photon therapy, wherein light beams are used in the absence of magnetic fields and physical massaging vibrations.

Magnetic therapy has been used for thousands of years around the world. Countries, including China, Japan, Russia, France and England have produced many documents on the subject. Around the world, magnetic therapy is considered a safe approach to healing. In the United States however, magnetic therapy is not generally considered a viable approach to healing. Nonetheless, some medical doctors in the United States have reported the use of static magnets to increase the speed at which bone fractures heal.

One area where magnetic technology has been extensively used in the United States is Magnetic Resonance Imaging (MRI) technology. An MRI device generates a magnetic field, in the order of tens of thousands of gauss, which is directed at a human body for exposing or producing images or pictures of anomalous areas. An MRI is not used as a curative or healing therapy. In contrast, the embodiments of the present invention generate magnetic fields less than ten gauss.

Recently issued U.S. Pat. No. 6,344,021 to Juster et al discloses that magnetic therapy speeds healing by boosting the body's synthesis of adenosine triphosphate (ATP). ATP is considered the fuel that fires all cellular processes and enhances the blood's ability to carry oxygen. Each individual cell possesses a positive electrical charge at its nucleus and a negative charge at its outer membrane. To properly function, the cells and nervous system rely on direct current (DC) and pulsed DC electrical energy. Consequently, life cannot exist without the flow of electricity. The '021 patent also reveals that static magnetic therapy requires lengthy periods of time (e.g., hours to days) before relief is realized by the patient. The embodiments of the present invention, however, utilize the specific combination of technologies to induce the flow of electricity in afflicted areas. Based on extensive clinical trials, patients have been relieved of chronic pain in seconds to minutes of treatment according to the embodiments of the present invention.

It is well known in the art that vibratory massage provides mechanical stimulation of tissues to increase blood flow to affected areas and enhance pain relief.

Laser light beams are routinely used in medical facilities for the treatment of a broad range of conditions including wound healing, edema reduction and post-operative pain relief. Light beams are directed to small areas or large areas of tissue depending on the condition and specific needs. For example, light beam therapy is routinely used in conventional medical hospital environments on newborn babies afflicted with yellow jaundice. Single lasers, multiple lasers, laser diodes and arrays are used to facilitate light beam therapy. U.S. Pat. No. 6,746,473 to Shanks and Tucek discloses the use of multiple laser diode sources providing a continuous beam and another beam producing a spot of pulsed laser light.

Sound waves have been used for centuries to both relax and stimulate human beings. This is one reason music has been popular since the dawn of mankind. Also, ultrasound technology is well known for therapeutic use to produce thermal and non-thermal effects.

BRIEF DESCRIPTION OF THE DRAWINGS

FIG. 1 shows a cross-section view along a length of a micro-vibration device of a first embodiment of the present invention;

FIG. 1A shows a cross-section along direction A;

DETAILED DESCRIPTION OF THE INVENTION

Figure 2:
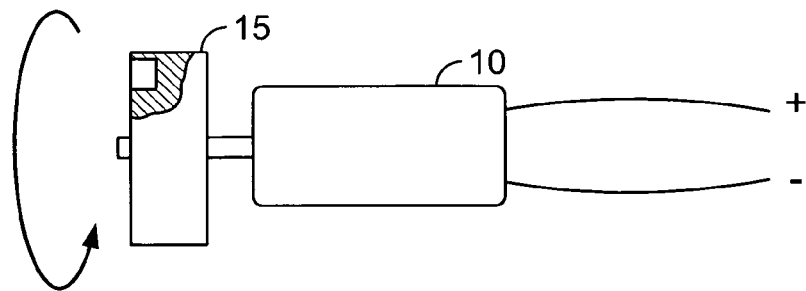
FIG. 2 shows a motor driving a magnet holder of the first embodiment the present invention.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

Applicants have developed a compact pain relief device and method of use for imparting various forms of energy to a human or animal. The device simultaneously provides multi-dimensional, horizontal, vertical and rotary, micro-vibration to selected areas of the body and therefore biological cells. The term "micro-vibration" as used herein shall refer to a rapid, reciprocating linear motion about an equilibrium position or a rapid symmetrical or asymmetric orbital motion about an axis, as well as any other suitable motion consistent with the known meaning of physical "vibration" in the field of physics. Micro-vibration may also be considered any mechanical, photonic, magnetic and sonic or acoustic vibration which, when the device is placed in contact with tissue, does not cause the tissue to move more than one-half millimeter in any direction.

Figure 3:
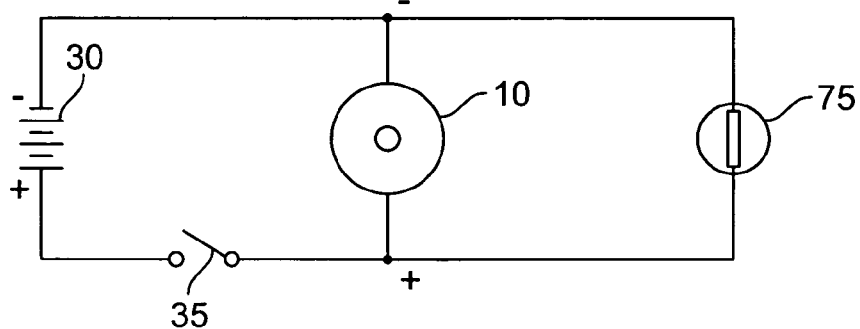
FIG. 3 is a schematic of an electrical circuit used to provide electrical power to micro-vibration device having one light source of the first embodiment of the present invention.

A first embodiment of the present invention is illustrated in FIGS. 1-3. The therapeutic device 5 comprises an electric motor 10 with a magnet holding fixture 15 attached to a motor shaft 20. Permanent magnet or electromagnet 25 is attached and held in place within holding fixture 15. As the permanent magnet or electromagnet 25 is connected to the shaft 20 in an offset manner, permanent magnet or electromagnet 25 is rotatably driven about the centerline of motor shaft 20 by motor 10. Depending on the use, the magnet 25 may be rotated at a constant or alternating rate of 500 to 150,000 revolutions per minute. Ideally, the intensity of the generated magnetic field is less than ten gauss. Importantly, the motor 10 should produce only a very small electromagnetic field so as not to interfere with the magnetic flux generated by the one or more permanent magnets or electromagnets 25. For example, the motor 10 may produce a magnetic or electromagnetic field with an intensity of less than 1% of that generated by the one or more magnets 25.

The motor 10 is powered by batteries 30 in response to electrical on-off switch 35 being turned on. As shown, the positive voltage (+) from batteries 30 flows through electrical conductor 40 to motor 10 and the negative voltage (−) flows through electrical conductor 45, battery holding cap 50, device enclosure 55, switch holding enclosure 60, enclosure embodiment 65 and motor holding fixture 70 to motor 10.

Photonic light is produced by one or more light sources 75, such as light bulbs. A laser or a light emitting diode may be used as well. Light sources 75 are electrically energized in a manner similar to motor 10. FIG. 1A shows a cross-section end view which details magnet 25 and multiple light sources 75. The light may fall into a broadband spectrum of light ranging from ultraviolet to infrared with optical light wavelengths ranging from about 1 nanometer (nm) to about 12,000 nm and the light sources 75 are directed into the magnetic field produced by magnet 25.

The combined magnetic field created by permanent magnet or electromagnet 25 and the photon electromagnetic field in the optical spectrum should not create any bulk heat in living cells. Accordingly, the photonic electromagnetic field in the optical light spectrum can be either continuously illuminating or pulsating such that the amplitude of the light intensity oscillates up and down in magnitude. In addition, the photonic electromagnetic field in the optical light spectrum may have either one or multiple discrete narrow bands of light of 30 nanometers (nm) or less in width that individually pulsate or change intensity amplitude by oscillating up and down in magnitude or become intermittent within the broadband light spectrum field.

The micro-vibration massage of the first embodiment of the present invention is produced by activating motor 10 to rotate the magnet holding fixture 15. The physical vibration, herein referred to as micro-vibration, is then transferred through motor holding fixture 70 and enclosure 65. The offset attachment of the permanent magnet or electromagnet magnet 25 to the shaft 20 creates oscillating inertial loads which are interpreted by human or animal senses as micro-vibration. When enclosure 65 is placed in contact with human or animal tissue, the micro-vibration is transferred to said tissue. In practice, the magnetic field produced by magnet or electromagnet 25 and the photonic electromagnetic field in the optical spectrum produced by light sources 75 are transferred to, and absorbed by, the body's cells as enclosure 65 is placed in contact with, or proximate to, the body. Running motor 10 and/or solid state sound generator (not shown) also produces an audible sonic sound that is likewise absorbed by the body. A sound transducer or voice coil speaker 80 is electrically driven in a manner similar to motor 10. The voice coil speaker 80 produces a soothing sound that is, as disclosed above, stimulating to human cells.

Figure 2A:
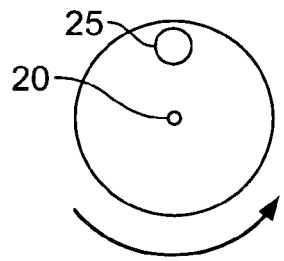
FIG. 2A shows an end view of the magnet holder of FIG. 2.
Figure 3A:
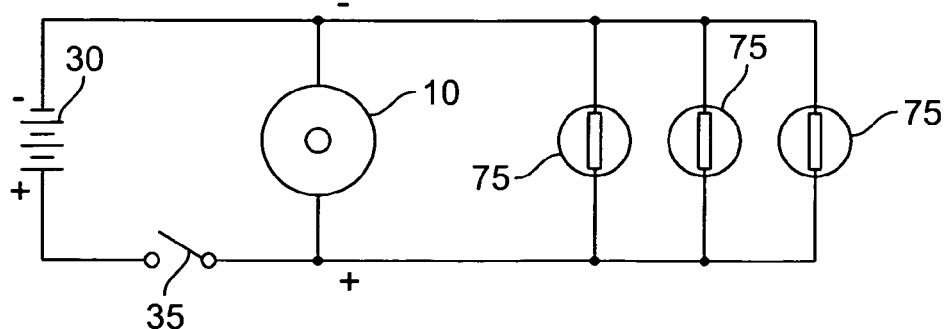
FIG. 3A is a schematic of an electrical circuit used to provide electrical power to micro-vibration device having multiple light sources of the first embodiment of the present invention.

FIGS. 2 and 2A illustrate the relationship between motor 10, magnet holding fixture 15 and magnet 25. Basically, the power source (e.g., batteries 30) drives the motor 10 that in turn rotates the magnet holding fixture 15 and contained magnet 25. FIGS. 3 and 3A illustrates an electrical schematic for the first embodiment of the present invention having one or multiple light sources 75, respectively. The schematic of FIG. 3 comprises a power source 30, motor 10, light source 75 and on-off switch 35. The schematic of FIG. 3A comprises a power source 30, motor 10, multiple light sources 75 and on-off switch 35.

It has been found that a small rotating magnetic field, as generated by a single rotating magnet, produces enhanced electron flow within cells being stimulated by light photons from the light sources 75. The synergistic effect increases the elimination of pain 5-10 times faster than photonic stimulation alone.

Figure 4:
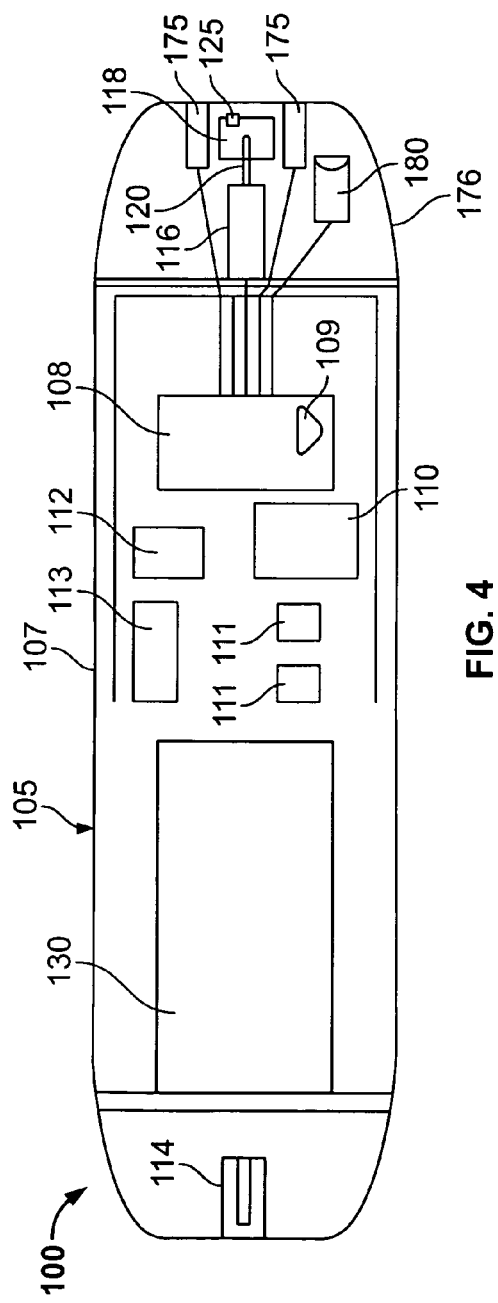
FIG. 4 shows a cross-section view along a length of a micro-vibration therapeutic device of a second embodiment of the present invention.
Figure 5:
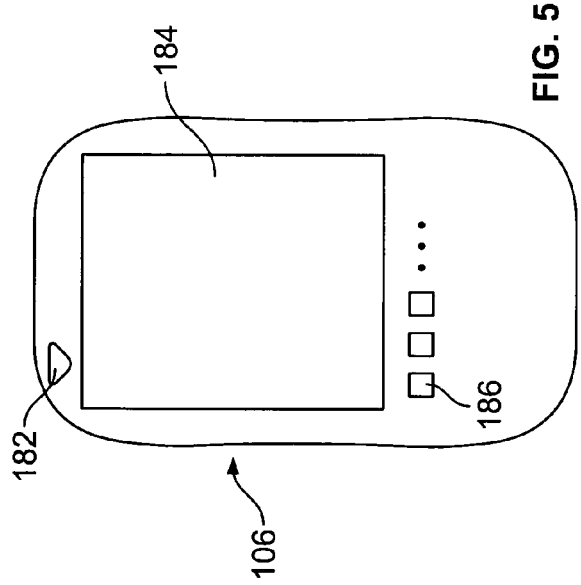
FIG. 5 shows a plan view of a controller suitable for use with the micro-vibration therapeutic device shown in FIG. 4.

Referring to FIGS. 4 and 5, in an alternative embodiment, a system 100 for relieving pain and providing a curative healing effect includes a handheld therapeutic device 105, as shown in FIG. 4, and a controller 106, as shown in FIG. 5, operatively coupled to, such as in signal communication with, therapeutic device 105. Controller 106 may include a computer or computer network (not shown) and/or handheld remote controller 106, as shown in FIG. 5, such as a cellular telephone or a personal data assistance device. In an alternative embodiment, controller 106 includes a desk mounted controller 106. Controller 106 includes suitable software configured to control, such as monitor and/or adjust, one or more parameters of therapeutic device 105, as described in greater detail below. Therefore, a technical effect according to one embodiment includes the capability of controlling operation of therapeutic device 105 through controller 106 including monitoring and/or adjusting one or more parameters of therapeutic device 105.

Controller 106 is in signal communication, such as through a wired connection or a wireless connection, with therapeutic device 105 and is configured to control operation of therapeutic device 105 to facilitate relieving pain and providing a curative healing effect. In one embodiment, controller 106 is in wireless signal communication with therapeutic device 105. A suitable radio frequency or digital technology is utilized to provide wireless signal communication between therapeutic device 105 and controller 106. In a particular embodiment, therapeutic device 105 and controller 106 are configured with suitable components such that controller 106 is in wireless signal communication with therapeutic device 105 over a suitable wireless personal area network (PAN), such as a Bluetooth™ wireless PAN, to facilitate exchange of information between controller 106 and therapeutic device 105. In this embodiment, controller 106 is in communication with therapeutic device 105 over a secure, short-range radio frequency. Controller 106 is configured to transmit command control signals to therapeutic device 105 as directed by a user, a physician, a nurse or a system technician. Further, controller 106 is configured to receive signals transmitted by therapeutic device 105 to facilitate monitoring and/or adjusting one or more parameters of therapeutic device 105 based, in one embodiment, at least partially on one or more signals transmitted by therapeutic device 105.

As shown in FIG. 4, therapeutic device 105 includes suitable components contained within a housing 107 of therapeutic device 105 to facilitate wireless communication with controller 106. In one embodiment, a Bluetooth™ module 108 including an antenna 109 is contained within housing 107 to facilitate signal communication between therapeutic device 105 and controller 106. Transmission of signals generated by Bluetooth™ module 108 and reception of signals by antenna 109 from controller 106 are processed by a Bluetooth™ controller 110 and/or one or more microcontrollers 111 contained within housing 107 and in operational control communication with Bluetooth™ module 108 and/or antenna 109 to facilitate signal communication between therapeutic device 105 and controller 106. Further, Bluetooth™ controller 110 and/or microcontroller 111 are configured to control one or more parameters of therapeutic device 105, as described below, based at least partially on the signal communication between therapeutic device 105 and control 106. In a particular embodiment, microcontroller 111 controls operation of therapeutic device 105, as described in greater detail below, based at least partially on command control signals received by Bluetooth™ module 108 from controller 106. In certain embodiments, a power charge 112 is operatively coupled to the Bluetooth™ wireless PAN components to provide suitable power for operation. Therapeutic device 105 may also include one or more serial ID controllers 113. In alternative embodiments, therapeutic device 105 and/or controller 106 include any suitable component, such as suitable PAN components in addition to or as an alternative to Bluetooth™ wireless PAN components, to facilitate wireless communication between therapeutic device 105 and controller 106.

Alternatively or in addition to wireless communication capability, therapeutic device 105 may be operatively coupled to controller 106 using a suitable wired communication component, such as a USB cable coupled to a cooperating USB port 114 of therapeutic device 105. It should be apparent to those skilled in the art and guided by the teachings herein provided that, in alternative embodiments, other suitable wired and/or wireless communication technologies and/or systems may be used to provide signal communication between therapeutic device 105 and controller 106.

Therapeutic device 105 includes an electric motor 116 with a magnet holding fixture 118 coupled to a motor shaft 120. At least one magnet 125, such as one or more permanent magnet or one or more electromagnet, is attached and held in place within magnet holding fixture 118. As magnet 125 is coupled to motor shaft 120 in an offset manner, magnet 125 is rotatably driven about a centerline of motor shaft 120 by motor 116 to generate a dynamic magnetic field which penetrates living tissue and generate micro-vibrations including oscillating inertial loads resulting from rotation of magnet 125 about the centerline. Depending on the use, magnet 125 may be rotated at a constant rate of rotation or an alternating rate rotation of about 500 revolutions per minute to about 150,000 revolutions per minute. In a particular embodiment, a plurality of magnets 125 are coupled to motor shaft 120 in an offset configuration such that magnets 125 rotate unevenly about a circle of rotation defined about the centerline of motor shaft 120. In one embodiment, an intensity of the generated magnetic field is less than ten gauss. Further, motor 116 produces only a very small electromagnetic field that does not interfere with the dynamic magnetic field generated by the one or more magnets 125. For example, motor 116 may produce a magnetic or electromagnetic field with an intensity of less than 1% of an intensity of a dynamic magnetic or electromagnetic field generated by the one or more magnets 125.

Motor 116 is powered by a power source, such as a suitable battery. In one embodiment, a battery 130, such as a rechargeable lithium battery or any suitable rechargeable battery, is positioned within housing 107 of therapeutic device 105. Referring to FIG. 4, battery 130 is operatively coupled to motor 116 to power motor 116. In one embodiment, battery 130 is activated to provide power to motor 116 in response to an electrical switch (not shown) being turned on. It should be apparent to those skilled in the art and guided by the teachings herein provided that any suitable power source including, without limitation, a charged or rechargeable battery may be utilized to power therapeutic device 105. In one embodiment, a light (not shown) or other suitable indicator indicates whether therapeutic device 105 is activated for operation or deactivated.

Therapeutic device 105 also includes at least one light source 175 for generating a photonic light field in an optical light spectrum. Light source 175 may include a light bulb, a laser or a light emitting diode, for example. Light source 175 is electrically energized by battery 130. Light emitted from light source 175 may fall into a broadband spectrum of light ranging from ultraviolet light to infrared light. In a particular embodiment, light source 175 produces the photonic light field in a broadband spectrum of light ranging from ultraviolet light to infrared light having optical light wavelengths ranging from about 1 nanometer (nm) to about 12,000 nm. In one embodiment, light source 175 directs emitted light into the magnetic field generated by magnet 125.

The combined magnetic field generated by magnet 125 and the photon electromagnetic field in the optical spectrum should not create any bulk heat in living cells. Accordingly, in one embodiment, the photonic electromagnetic field in the optical light spectrum can be either continuously illuminating or pulsating such that an amplitude of the light intensity oscillates up and down in magnitude. In addition, the photonic electromagnetic field in the optical light spectrum may have either one or multiple discrete narrow bands of light of 30 nanometers (nm) or less in width that individually pulsate or change intensity amplitude by oscillating up and down in magnitude or become intermittent within the broadband light spectrum field.

The micro-vibration massage of the alternative embodiment shown in FIG. 4 is produced by activating motor 116 to rotate magnet holding fixture 118. The physical vibration, herein referred to as micro-vibration, is then transferred through an enclosure 176. The offset attachment of magnet 125 to motor shaft 120 creates oscillating inertial loads which are interpreted by human or animal senses as micro-vibration. When enclosure 176 is placed in contact with human or animal tissue, the micro-vibration is transferred to the tissue. In practice, the magnetic field produced by magnet 125 and the photonic electromagnetic field in the optical spectrum produced by light sources 175 are transferred to, and absorbed by, the body's cells as enclosure 176 is placed in contact with, or proximate to, the body. Running motor 116 and/or a solid state sound generator (not shown) also produces an audible sonic sound that is likewise absorbed by the body. A sound transducer or voice coil speaker 180 or other suitable component configured to produce audible acoustic tones is electrically driven by battery 130 in a manner similar to motor 116. Speaker 180 produces a soothing sound that is, as disclosed above, relaxing and soothing to human senses and stimulating to human cells. Alternatively or in addition, motor 116 produces audible acoustic tones.

It has been found that a small rotating magnetic field, as generated by one or more rotating magnets 125, produces enhanced electron flow within cells being stimulated by light photons from one or more light sources 175. The synergistic effect increases the elimination of pain 5-10 times faster than photonic stimulation alone. Therapeutic device 105 produces microvibratory, electromagnetic, photon, biochemical stimulation that induces a change in cellular energy. More specifically, the magnetic field generated by the rotating magnet(s) 125 alters cellular energy in living organisms. In one embodiment, the magnetic, photon, vibration and/or sonic sound wave technologies results in a reduction in pain in less than five minutes.

Referring further to FIG. 5, handheld or desk mounted remote controller 106 includes an antenna 182 to facilitate signal communication with Bluetooth™ module 108 through antenna 109. Controller 106 also includes a display screen 184 configured to display icons and/or text, such as icons and/or text representative of command control signals generated by controller 106 and transmitted to therapeutic device 105 and/or signals generated and transmitted by therapeutic device 105 to controller 106 representative of one or more parameter values of therapeutic device 105. Further, controller 106 includes a plurality of inputs 186, such as touch screen inputs, keys and/or knobs, configured to facilitate transmitting command control signals to therapeutic device 105. It should be apparent to those skilled in the art and guided by the teachings herein provided that any suitable display screen and/or number and/or type of input may be utilized to facilitate communication between therapeutic device 105 and handheld or desk mounted remote controller 106.

As described above, controller 106 is configured to transmit command control signals to therapeutic device 105 to control one or more parameters of therapeutic device 105. In a particular embodiment, controller 106 is configured to activate and/or adjust therapeutic device 105, activate and/or adjust motor 116 to rotate one or more magnets 125 at an alternating rate of rotation or a constant rate of rotation, adjust a light intensity of one or more light sources 175 and/or a number of light sources 175 emitting light, and activate and/or adjust speaker 180 for producing acoustic tones, as described above, for example.

Figure 6:
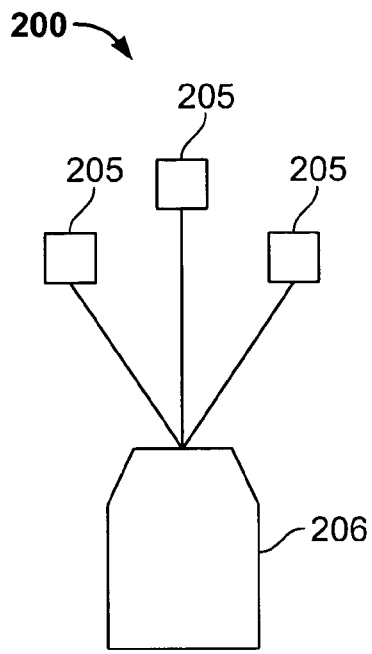
FIG. 6 shows a schematic view of a micro-vibration system including a plurality of therapeutic modules operatively coupled to a controller.
Figure 7:
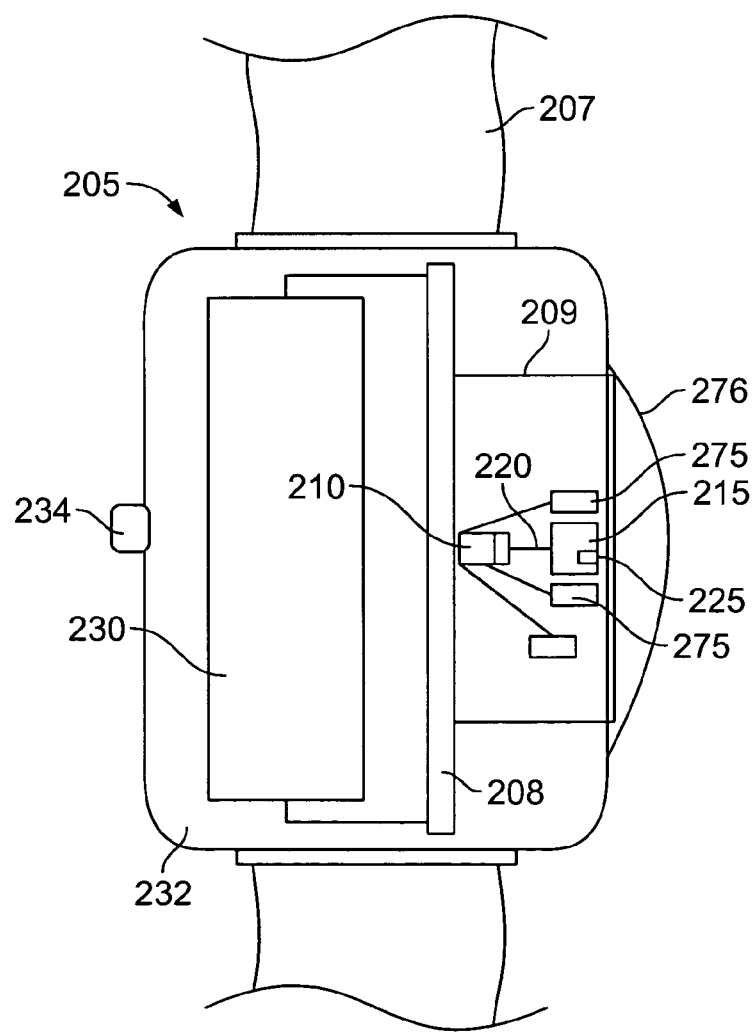
FIG. 7 shows a cross-section view along a length of the therapeutic module shown schematically in FIG. 6.
Figure 8:
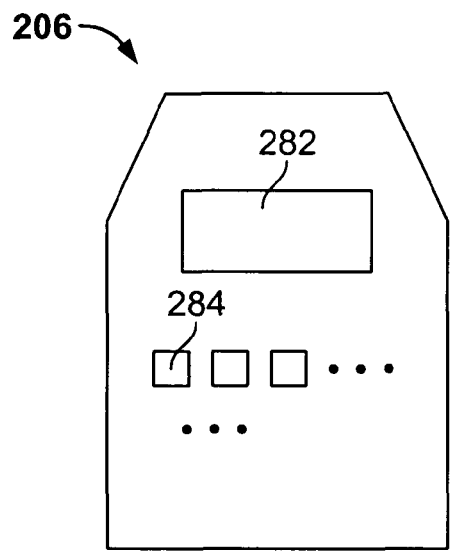
FIG. 8 shows a plan view of the controller shown schematically in FIG. 6 and suitable for use with the therapeutic module shown in FIG. 7.

Referring to FIGS. 6-8, in a further alternative embodiment a system 200 for relieving pain and providing a curative healing effect includes at least one handheld therapeutic module 205 and a controller 206 operatively coupled to each therapeutic module 205. It should be apparent to those skilled in the art and guided by the teachings herein provided that system 200 may include any suitable number of therapeutic modules 205 each independently coupled to controller 206 to facilitate relieving pain and providing a curative healing effect. Controller 206 may include a computer or computer network (not shown) and/or handheld remote controller 206, as shown in FIG. 8, such as a cellular telephone or a personal data assistance device. In an alternative embodiment, controller 206 includes a desk mounted controller 206. Controller 206 includes suitable software configured to control, such as monitor and/or adjust, one or more parameters of therapeutic module 205, as described in greater detail below. Therefore, a technical effect according to one embodiment includes the capability of controlling operation of each therapeutic module 205 through controller 206 including monitoring and/or adjusting one or more parameters of therapeutic module 205.

Controller 206 is in signal communication, such as through a wired connection or a wireless connection, with each therapeutic module 205 and is configured to independently control operation of each therapeutic module 205 to facilitate relieving pain and providing a curative healing effect. In one embodiment, controller 206 is in wireless signal communication with each therapeutic module 205, as shown in FIGS. 6-8. A suitable radio frequency or digital technology is utilized to provide wireless signal communication between each therapeutic module 205 and controller 206. In a particular embodiment, controller 206 is in wireless signal communication with each therapeutic module 205 over a suitable wireless personal area network (PAN), such as a Bluetooth™ wireless PAN described above in reference to system 100, to facilitate exchange of information between controller 206 and each therapeutic module 205. In this embodiment, controller 206 is in communication with each therapeutic module 205 over a secure, short-range radio frequency. In alternative embodiments, therapeutic module 205 and/or controller 206 include any suitable component, such as suitable PAN components in addition to or as an alternative to Bluetooth™ wireless PAN components, to facilitate wireless communication between therapeutic module 205 and controller 206.

Controller 206 is configured to transmit command control signals to each therapeutic module 205 as directed by a user, a physician, a nurse or a system technician. Further, controller 206 is configured to receive signals transmitted by each therapeutic module 205 to facilitate monitoring and/or adjusting one or more parameters of the corresponding therapeutic module 205 based, in one embodiment, at least partially on one or more signals transmitted by the corresponding therapeutic module 205. Each therapeutic module 205 includes a powered circuit board (PCB) 208 to facilitate signal communication between therapeutic module 205 and control 206 and/or controlling one or more parameters of therapeutic module 205, as described below, based at least partially on the signal communication between therapeutic module 205 and control 206.

Alternatively, each therapeutic module 205 may be operatively coupled to controller 206 using a suitable wired communication component, such as a USB cable coupled to cooperating USB ports (not shown in FIGS. 6-8) of therapeutic module 205 and controller 206. It should be apparent to those skilled in the art and guided by the teachings herein provided that other suitable wired and/or wireless communication technologies and/or systems may be used to provide signal communication between therapeutic module 205 and controller 206.

Referring further to FIG. 7, each therapeutic module 205 includes a suitable strap 207 and/or other suitable fastening component to facilitate retaining therapeutic module 205 at a desired position or location with respect to the patient's body. For example, with therapeutic module 205 positioned on a forearm of the patient, strap 207 may be positioned about the patient's arm to retain therapeutic module 205 properly positioned at the desired location on the forearm. As shown in FIG. 7, each therapeutic module 205 includes a module housing 209 configured to contain an electric motor 210 with a magnet holding fixture 215 coupled to a motor shaft 220. At least one magnet 225, such as one or more permanent magnet or one or more electromagnet, is coupled and held in place within magnet holding fixture 215. As magnet 225 is coupled to motor shaft 220 in an offset manner, magnet 225 is rotatably driven about a centerline of motor shaft 220 by motor 210 to generate a dynamic magnetic field which penetrates living tissue and generate micro-vibrations including oscillating inertial loads resulting from rotation of magnet 225 about the centerline. Depending on the use, magnet 225 may be rotated at a constant rate of rotation or an alternating rate of rotation of about 500 revolutions per minute to about 150,000 revolutions per minute. In a particular embodiment, a plurality of magnets 225 are coupled to shaft 220 in an offset configuration such that magnets 225 rotate unevenly about a circle of rotation defined about the centerline of shaft 220. In one embodiment, an intensity of the generated magnetic field is less than 10 gauss. Further, motor 210 produces only a very small magnetic field that does not interfere with the dynamic magnetic field generated by the one or more magnets 225. For example, motor 210 produces a magnetic or electromagnetic field with an intensity of less than 1% of an intensity of a dynamic magnetic or electromagnetic field generated by the one or more magnets 225.

Motor 210 is powered by a power source, such as a suitable battery. In one embodiment, a battery 230, such as a rechargeable lithium battery or any suitable rechargeable battery, is positioned within a housing 232 of therapeutic module 205. It should be apparent to those skilled in the art and guided by the teachings herein provided that any suitable power source including, without limitation, a charged or rechargeable battery may be utilized to power each therapeutic module 205. In one embodiment, a light 234 or other suitable indicator indicates whether therapeutic module 205 is activated for operation or deactivated.

Therapeutic module 205 also includes at least one light source 275 for generating a photonic light field in an optical light spectrum. Light source 275 may include a light bulb, a laser or a light emitting diode, for example. Light source 275 is electrically energized by battery 230. Light emitted from light source 275 may fall into a broadband spectrum of light ranging from ultraviolet light to infrared light. In a particular embodiment, light source 275 produces the photonic light field in a broadband spectrum of light ranging from ultraviolet light to infrared light having optical light wavelengths ranging from about 1 nanometer (nm) to about 12,000 nm. In one embodiment, light source 275 directs emitted light into the magnetic field generated by magnet 225.

The combined magnetic field generated by magnet 225 and the photon electromagnetic field in the optical spectrum should not create any bulk heat in living cells. Accordingly, in one embodiment, the photonic electromagnetic field in the optical light spectrum can be either continuously illuminating or pulsating such that an amplitude of the light intensity oscillates up and down in magnitude. In addition, the photonic electromagnetic field in the optical light spectrum may have either one or multiple discrete narrow bands of light of 30 nanometers (nm) or less in width that individually pulsate or change intensity amplitude by oscillating up and down in magnitude or become intermittent within the broadband light spectrum field.

The micro-vibration massage of the alternative embodiment shown in FIG. 7 is produced by activating motor 210 to rotate magnet holding fixture 215. The physical vibration, herein referred to as micro-vibration, is then transferred through an enclosure 276. The offset attachment of magnet 225 to motor shaft 220 creates oscillating inertial loads which are interpreted by human or animal senses as micro-vibration. When enclosure 276 is placed in contact with human or animal tissue, the micro-vibration is transferred to the tissue. In practice, the magnetic field produced by magnet 225 and the photonic electromagnetic field in the optical spectrum produced by light sources 275 are transferred to, and absorbed by, the body's cells as enclosure 276 is placed in contact with, or proximate to, the body. Running motor 210 and/or a solid state sound generator (not shown) also produces an audible sonic sound that is likewise absorbed by the body. In one embodiment, a sound transducer or voice coil speaker 280 or other suitable component configured to produce audible acoustic tones is electrically driven by battery 230 in a manner similar to motor 210. Speaker 280 produces a soothing sound that is, as disclosed above, relaxing and soothing to human senses and stimulating to human cells. Alternatively or in addition, motor 210 produces audible acoustic tones.

It has been found that a small rotating magnetic field, as generated by one or more rotating magnets 225, produces enhanced electron flow within cells being stimulated by light photons from one or more light sources 275. The synergistic effect increases the elimination of pain 5-10 times faster than photonic stimulation alone. Therapeutic module 205 produces microvibratory, electromagnetic, photon, biochemical stimulation that induces a change in cellular energy. More specifically, the magnetic field generated by the rotating magnet(s) 225 alters cellular energy in living organisms. In one embodiment, the magnetic, photon, vibration and/or sonic sound wave technologies results in a reduction in pain in less than five minutes.

Referring further to FIG. 8, handheld or desk mounted remote controller 206 includes a display screen 282 configured to display icons and/or text, such as icons and/or text representative of command control signals generated by controller 206 and transmitted to therapeutic module 205 and/or signals generated and transmitted by therapeutic module 205 to controller 206 representative of one or more parameter values of therapeutic module 205. Further, controller 206 includes a plurality of inputs 284, such as touch screen inputs, keys and/or knobs, configured to facilitate transmitting command control signals to therapeutic module 205. It should be apparent to those skilled in the art and guided by the teachings herein provided that any suitable display screen and/or number and/or type of input may be utilized to facilitate communication between therapeutic module 205 and controller 206.

As described above, controller 206 is configured to transmit command control signals to therapeutic module 205 to control one or more parameters of therapeutic module 205. In a particular embodiment, controller 206 is configured to activate and/or adjust therapeutic module 205, activate and/or adjust motor 210 to rotate magnet 225 at an alternating rate of rotation or a constant rate of rotation, adjust a light intensity of light source 275 and/or a number of light sources 275 emitting light, and activate and/or adjust speaker 280 for producing acoustic tones, as described in greater detail above, for example.

Figure 9:
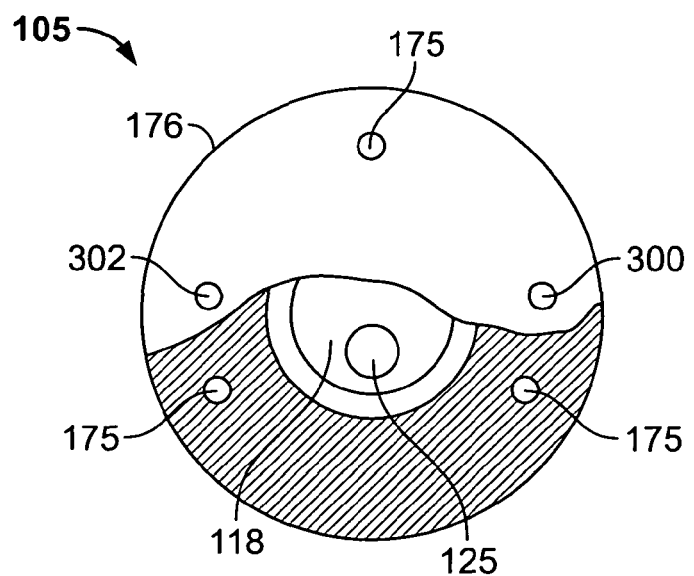
FIG. 9 shows a front view of the micro-vibration therapeutic device shown in FIG. 4.

In one embodiment, therapeutic device 105 is configured to generate a microcurrent to provide transcuteneous electrical stimulation therapy. As shown in FIG. 9, a positive terminal 300 and a negative terminal 302 are each operative coupled to battery 130 (not shown in FIG. 9) such that, with enclosure 176 contacting a patient's skin, a microcurrent flows along a path defined by the resulting electric circuit. In a particular embodiment, the microcurrent of less than about 1 milliampere is generated between positive terminal 300 and negative terminal 302 to facilitate providing transcuteneous electrical stimulation therapy for administering pain relief.

In one embodiment, a method for administering pain relief with at least one therapeutic module includes rotating at least one magnet to generate a magnetic field. The magnetic field includes a moving circular magnetic field pattern with a centerline of the magnetic field parallel to a centerline of a rotating shaft coupling the at least one magnet to a motor. A photonic light field is generated in an optical light spectrum producing light having an optical light wavelength ranging from about 1 nanometer to about 12,000 nanometers. In a particular embodiment, the photonic light field is directed into the magnetic field. Additionally, micro-vibrations are generated by rotating the at least one magnet coupled to the shaft in an offset configuration in a circular pattern defined about a centerline of the shaft. A magnetic field is generated by rotating the at least one magnet at an alternating rate or a constant rate between about 500 revolutions per minute and about 150,000 revolutions per minute. In a particular embodiment, audible acoustic tones that soothing are also generated by the therapeutic module. The at least one therapeutic module is placed in contact with, or proximate to, a pain area on a human or animal body. In one embodiment, upon contact with the at least one therapeutic module, a compliant surface of the body does not move more than one-half millimeter in a direction as a result of the generated micro-vibrations. Further, the magnetic field, the photonic optical light field and micro-vibrations do not produce bulk heating formed in living cells or tissue.

A controller is operatively coupled to each therapeutic module. The controller may include a computer and/or a handheld or desk mounted controller that includes software configured to control one or more parameters of each therapeutic module.

The present disclosure describes a therapeutic micro-vibration massaging device that generates a dynamic magnetic field and an electromagnetic photonic light field, accompanied by audible acoustic sound, that penetrate the human body, induce an increase in cellular energy and thereby promote a curative healing effect that reduces or eliminates pain.

While the invention has been described in terms of various specific embodiments, those skilled in the art will recognize that the invention can be practiced with modification within the spirit and scope of the claims.

What is claimed is:

1. A therapeutic module for relieving pain and providing a curative healing effect, said therapeutic module comprising:
   a motor for rotating at least one magnet to generate a magnetic field, micro-vibrations and audible acoustic tones;
   a shaft coupling said at least one magnet to said motor, said at least one magnet coupled to said shaft in an offset configuration with respect to a centerline of said shaft thereby generating micro-vibrations in the form of oscillating inertial loads; and
   a light source for generating a photonic light field in an optical light spectrum.

2. A therapeutic module in accordance with claim 1 wherein said at least one magnet comprises one or more of the following: a permanent magnet and an electromagnet.

3. A therapeutic module in accordance with claim 1 wherein said at least one magnet comprises a plurality of magnets coupled to said shaft in an offset configuration such that said plurality of magnets rotate unevenly about a circle of rotation defined about the centerline of said shaft.

4. A therapeutic module in accordance with claim 1 further comprising a speaker configured to produce audible acoustic tones to facilitate relieving pain and providing a curative healing effect.

5. A therapeutic module in accordance with claim 1 further comprising an electronic circuit board coupled in control communication with said motor, said electronic circuit board configured to control one or more parameters of said therapeutic module.

6. A therapeutic module in accordance with claim 5 wherein said electronic circuit board is configured to control at least one of activating said motor to rotate said at least one magnet, a rate of rotation of said at least one magnet at one of an alternating rate and a constant rate, a light intensity of said light source, a number of light sources emitting light, and said speaker for producing acoustic tones.

7. A therapeutic module in accordance with claim 1 further comprising a power source positioned within a housing of said therapeutic module, said power source operatively coupled to said motor.

8. A therapeutic module in accordance with claim 1 wherein said light source produces a photonic light field in a broadband spectrum of light ranging from ultraviolet to infrared having optical light wavelengths of about 1 nanometer to about 12,000 nanometers.

9. A therapeutic module in accordance with claim 1 wherein said motor generates micro-vibrations such that, upon contact with said therapeutic module, a compliant surface does not move more than one-half millimeter in a direction.

10. A therapeutic module in accordance with claim 1 wherein said magnetic field and said photonic light field do not produce bulk heating in living cells or tissue.

11. A therapeutic module in accordance with claim 1 wherein said magnetic field is no more than ten gauss in field intensity.

12. A therapeutic module in accordance with claim 1 wherein said magnetic field is created by rotating said at least one magnet at one of an alternating rate and a constant rate between about 500 and about 150,000 revolutions per minute.

13. A therapeutic module in accordance with claim 1 wherein said therapeutic module produces vibratory, magnetic, photon and biochemical stimulation that induce a change in cellular energy.

14. A therapeutic module in accordance with claim 1 wherein said magnetic field alters cellular energy in living organisms.

15. A therapeutic module in accordance with claim 1 wherein at least one of micro-vibration, magnetic, photon, audible and acoustic sound wave technologies produces a reduction in pain in less than five minutes.

16. A therapeutic module in accordance with claim 1 wherein said motor produces a magnetic field that does not interfere with said dynamic magnetic field generated by said at least one magnet, said motor producing the magnetic field not greater than 1% of said dynamic magnetic field generated by said at least one magnet.

17. A therapeutic module in accordance with claim 1 further comprising a fastening component to facilitate retaining said therapeutic module at a desired location with respect to a patient body.

18. A system for relieving pain and providing a curative healing effect comprising:
   at least one therapeutic module comprising:
      at least one magnet coupled to a shaft in an offset configuration with respect to a centerline of said shaft;
      a motor coupled to said shaft for rotatably driving said at least one magnet to generate a dynamic magnetic field which penetrates living tissue and micro-vibrations comprising oscillating inertial loads resulting from rotation of said at least one magnet about the centerline; and
      a light source for generating a photonic light field in an optical light spectrum; and
   a controller operatively coupled to said at least one therapeutic module, said controller configured to control said at least one therapeutic module to facilitate relieving pain and providing a curative healing effect.

19. A system in accordance to claim 18 wherein said at least one therapeutic module further comprises a speaker configured to produce audible acoustic tones.

20. A system in accordance with claim 18 wherein said at least one magnet comprises one of a permanent magnet and an electromagnet.

21. A system in accordance with claim 18 wherein said at least one magnet comprises a plurality of magnets coupled to said shaft in an offset configuration such that said plurality of magnets rotate unevenly about a circle of rotation defined about the centerline of said shaft.

22. A system in accordance with claim 18 comprising a plurality of therapeutic modules.

23. A system in accordance with claim 18 wherein said controller coupled is configured to control one or more parameters of said at least one therapeutic module.

24. A system in accordance with claim 23 wherein said controller is configured to control at least one of activating said motor to rotate said at least one magnet, a rate of rotation of said at least one magnet at one of an alternating rate and a constant rate, a light intensity of said light source, a number of light sources emitting light, and a speaker for producing acoustic tones.

25. A system in accordance with claim 18 wherein said controller comprises one of a remote control and a computer.

26. A system in accordance with claim 18 wherein said controller is operatively coupled to said at least one therapeutic module via at least one of a wired connection and a wireless connection.

27. A system in accordance with claim 18 wherein said light source produces the photonic light field in a broadband spectrum of light ranging from ultraviolet to infrared having optical light wavelengths from about 1 nanometer to about 12,000 nanometers.

28. A system in accordance with claim 18 wherein said magnetic field is created by rotating said at least one magnet at one of an alternating rate and a constant rate between about 500 and about 150,000 revolutions per minute.

29. A system in accordance with claim 18 wherein said audible acoustic tones are relaxing and soothing to human senses.

30. A system in accordance with claim 18 wherein said at least one therapeutic module produces microvibratory, electromagnetic, photon, biochemical stimulation that induces a change in cellular energy.

31. A system in accordance with claim 18 wherein said magnetic field alters cellular energy in living organisms.

32. A system in accordance with claim 18 wherein at least one of magnetic, photon, vibration and sonic sound wave technologies results in a reduction in pain in less than five minutes.

33. A system in accordance with claim 18 wherein at least one of said motor and a speaker produces audible acoustic tones.

34. A method for administering pain relief with at least one therapeutic module, said method comprising:
   rotating at least one magnet to generate a magnetic field, the magnetic field comprising a moving circular magnetic field pattern with a centerline of the magnetic field parallel to a centerline of a rotating shaft coupling the at least one magnet to a motor;
   generating a photonic light field in an optical light spectrum, the photonic light field directed into the magnetic field;
   generating micro-vibrations by rotating the at least one magnet coupled to the shaft in an offset configuration in a circular pattern defined about a centerline of the shaft;
   generating audible acoustic tones; and
   placing the at least one therapeutic module in contact with, or proximate to, a pain area on a human or animal body.

35. A method in accordance with claim 34 further comprising operatively coupling the at least one therapeutic module to a controller.

36. A method in accordance with claim 35 wherein the therapeutic module is operatively coupled to one of a computer and a controller comprising software configured to control one or more parameters of the at least one therapeutic module.

37. A method in accordance with claim 34 further comprising producing optical light wavelengths ranging from about 1 nanometer to about 12,000 nanometers.

38. A method in accordance with claim 34 further comprising generating micro-vibrations such that, upon contact with the at least one therapeutic module, a compliant surface does not move more than one-half millimeter in a direction.

39. A method in accordance with claim 34 further comprising producing the magnetic field and the photonic optical light field and micro-vibrations such that no bulk heating is formed in living cells or tissue.

40. A method in accordance with claim 34 further comprising generating the magnetic field by rotating the at least one magnet at one of an alternating rate and a constant rate between about 500 and about 150,000 revolutions per minute.

\* \* \* \* \*